United States Patent [19]
Hosono

[11] 3,998,216
[45] Dec. 21, 1976

[54] BENDING TUBE FOR ENDOSCOPE
[75] Inventor: Saburo Hosono, Tokyo, Japan
[73] Assignee: Olympus Optical Company Ltd., Tokyo, Japan
[22] Filed: Oct. 2, 1974
[21] Appl. No.: 511,249

[30] Foreign Application Priority Data
  Oct. 4, 1973  Japan ............................ 48-111756
[52] U.S. Cl. .................................................. 128/6
[51] Int. Cl.² .......................................... A61B 1/06
[58] Field of Search .................................. 128/4–6, 128/349 R

[56] References Cited
UNITED STATES PATENTS

| | | | |
|---|---|---|---|
| 3,669,098 | 6/1972 | Takahashi | 128/6 |
| 3,670,721 | 6/1972 | Fukami et al. | 126/6 |
| 3,788,304 | 1/1974 | Takahashi | 126/6 |

FOREIGN PATENTS OR APPLICATIONS 2,150,595  4/1972  Germany ............................... 128/4

Primary Examiner—Lawrence Charles

[57] ABSTRACT

A bending tube extends between the flexible tube and the distal end portion of an endoscope, and is subject to a bending control from the control unit of the endoscope for swinging the distal end portion in a desired direction. The bending tube comprises a braided structure and an outer framework. The resulting construction permits the bending tube to bend freely in all directions and prevents the outer shell from being damaged by the framework and also increases the interior space of the bending tube.

4 Claims, 14 Drawing Figures

BENDING TUBE FOR ENDOSCOPE

BACKGROUND OF THE INVENTION

The invention relates to an improvement of a bending tube used in an endoscope.

An endoscope is designed for insertion of its distal end portion into internal organs of a human body such as stomach or intestines so that the condition of a part to be examined may be visually observed through an observation window formed in the distal end portion and an eyepiece assembly mounted on a control unit which remains outside the human body. The control unit and the distal end portion are interconnected by a flexible tube which includes a bending tube at its juncture with the distal end portion. It is not intended that the flexible portion or tube be positively controlled for bending by an operation of the control unit even though it is free to flex along the curved walls of the internal organs. By contrast, the bending tube is subject to a two- or three-dimensional bending by an operation of the control unit in order to swing the distal end portion so that the observation window therein may be easily directed toward a part to be examined.

It is necessary that the bending tube houses a number of internal components such as optical fibre bundles and/or forceps conduit internally, and this requires that the bending tube be as simple and thin a structure as might be desired and have a satisfactory bending strength.

Most conventional bending tubes comprise a framework covered with a braided work which is in turn covered with an outer shell. Such structures often caused accidents whereby the framework may damage the braided work or outer shell or even pierce therethrough. In addition, a conventional bending tube is thick-walled resulting in a decrease in the internal space available, and is also limited in the degree of bending because of the tube structure.

SUMMARY OF THE INVENTION

It is an object of the invention to provide a bending tube for endoscopes which eliminates the inconveniences or drawbacks associated with the prior art structure by using a braided structure and a skeleton located within a framework.

The bending tube for endoscopes constructed in accordance with the invention is simple in construction, easy to manufacture, and has a high bending strength which is achieved by using an outer framework. Specifically, the framework and the inner braided structure co-operate to resist a longitudinal compression of the tube and a torsion about the axis of the tube and to assist in avoiding a serpentine configuraton of the bending tube. Since the framework is located outside the braided structure, no damage of the latter is caused by the former while preventing the braided structure from constraining the movement of the framework. Substantially no structural component is present inside the braided structure, thus increasing the available internal space for a given outer diameter and allowing the diameter of the endoscope to be reduced.

DETAILED DESCRIPTION OF A PREFERRED EMBODIMENT

Figure 1:
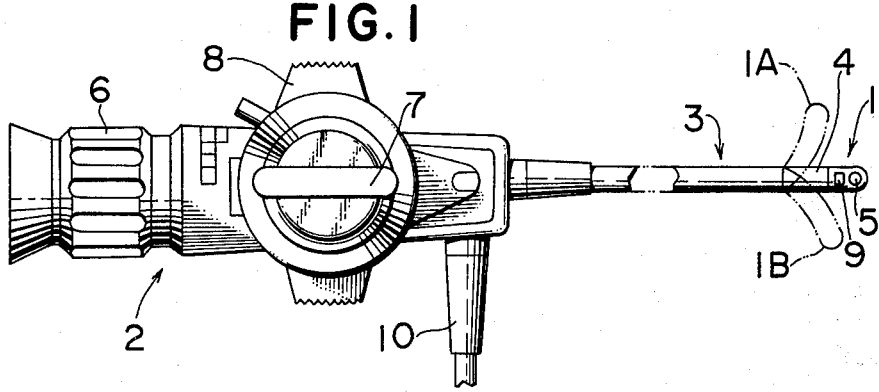
FIG. 1 is a plan view showing the geneeral arrangement of an endoscope to which the invention is applied.

Referring to FIG. 1, there is shown an endoscope constructed in accordance with the invention. The endoscope includes a distal end portion 1 and a control unit 2 which are physically connected together by a flexible tube 3 including a bending tube 4 which is constructed in accordance with the invention. The distal end portion 1 includes an observation window 5 which is optically coupled with an eyepiece assembly 6 mounted on the control unit 2 through a bundle of optical fibres, not shown. The control unit 2 further includes flexure operating knobs 7 and 8 which are connected with the proximate end of the distal end portion 1 through operating wires, not shown, which may be operated by means of the knobs 7 and 8 so as to swing the distal end portion 1 in a three dimensional manner to positions 1A and 1B shown in phantom line as well as to an orientation which is normal to the plane of the drawing. Under certain situations, it may be sufficient to have a two-dimensional swinging motion of the distal end portion 1, which may be accomplished by the use of a single operating knob. The distal end portion 1 additionally includes an illumination window 9 which may be coupled with a light source, not shown, through a bundle of optical fibres, also not shown, which in turn may extend through the flexible tube 3 for connection with a branch pipe 10 mounted on the control unit 2.

Figure 2:
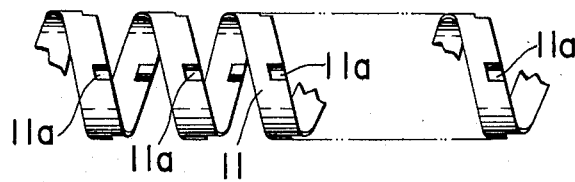
FIG. 2 is a side elevation of one example of flex used as a skeleton in the invention.
Figure 3:
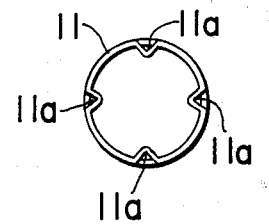
FIG. 3 is a front view of the flex shown in FIG. 2.
Figure 4:
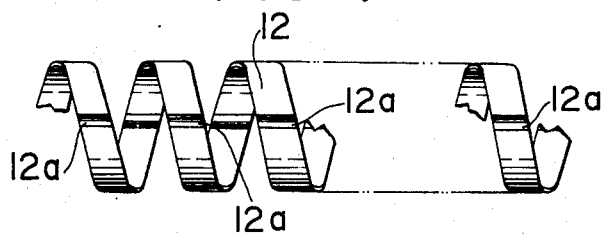
FIG. 4 is a side elevation of another example of flex used as a skeleton.
Figure 5:
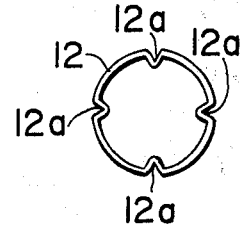
FIG. 5 is a front view of the flex shown in FIG. 4.

Referring to FIGS. 2 and 3, there is shown in greater detail an example of a flex 11 which constitutes a skeleton for the bending tube 4 shown in FIG. 1. The flex 11 comprises a metal or plastic strip formed into a helical pattern, with four depressions 11a formed at equispaced intervals per turn of the helical pattern. In FIGS. 2 and 3, these depressions are formed by providing a cut in the strip and then depressing the strip material inwardly. However, in a flex 12 shown in FIGS. 4 and 5, these depressions extend across the full width of the strip.

Figures 6, 7, 8, 9:
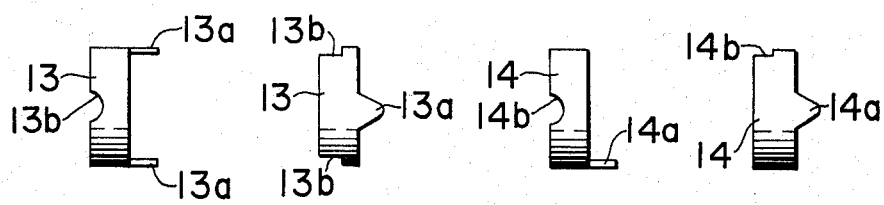
FIGS. 6 to 9 are side elevations showing several examples of a framework.

FIGS. 6 and 7 show a frame member 13 used in forming the bending tube 4 of the invention. The member 13 is annular in cross-sectional configuraton. Along its one end edge, the member 13 is formed with a pair of diametrically opposite projections 13a, while it is formed with recesses 13b along its other edge at substantially median positions intermediate the projections 13a. Members 13 are juxtaposed with each other with projections 13a and recesses 13b of adjacent members in engagement so as to produce a framework. It is to be understood that the member 13 shown in FIGS. 6 and 7 may be replaced by a member 14 illustrated in FIGS. 8 and 9 which includes a single projection 14a and a single recess 14b, which are spaced apart by substantially one-quarter of the perimeter.

Figure 10:
FIG. 10 is a side elevation of an example of a braided structure.
Figure 11:
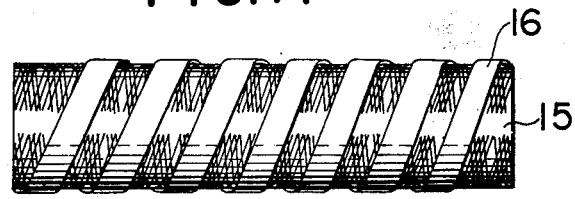
FIG. 11 is a side elevation showing a combination of a braided structure and a flex used as an outer framework.
Figure 12:
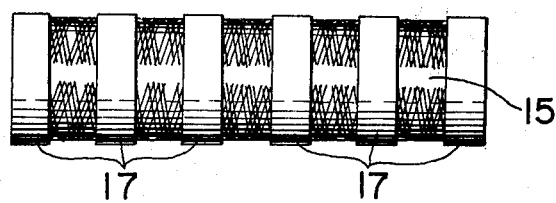
FIG. 12 is a side elevation showing a combination of a braided structure and a hollow cylinder used as an outer framework.

FIG. 10 shows a braided structure 15 used in forming the bending tube 4 of the invention. The structure 15 comprises a hollow cylinder braided with thin wires of metal or synthetic resin, but may be either twilled, satin or plain woven. Preferably the wire elements are woven in a crosswise pattern around the axis of the braided structure 15 to impart flexibility thereto. FIG. 11 shows a combination of the braided structure 15 with a flex 16 as a framework. The bending tube 4 according to the invention is completed by applying an outer shell or sleeve (not shown) of plastic or similar material thereover. In FIG. 12, a plurality of hollow cylinders 17 are used in place of the flex 16, and this can be satisfactory. Flex 11 or 12 will be referred to herein as a skeleton.

Figure 13:
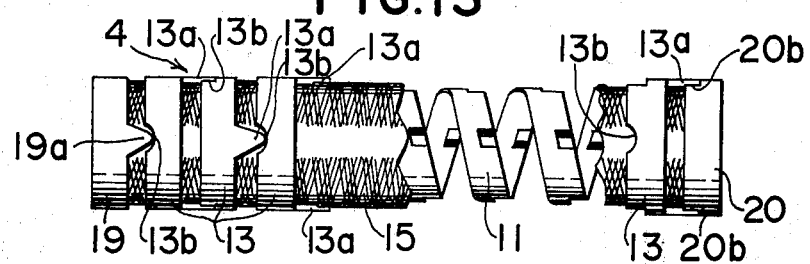
FIG. 13 is a side elevation, partially broken away, of the bending tube constructed according to one embodiment of the invention.
Figure 14:
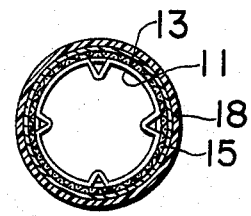
FIG. 14 is a front view of the bending tube of FIG. 13.

FIGS. 13 and 14 show another embodiment of the bending tube 4 according to the invention, comprising the flex 11, the braided structure 15 applied over the flex 11, and a framework formed by frame members 13 joined successively at their projections 13a and recesses 13b, with an outer shell 18 (see FIG. 14) of a plastic material applied over the framework. The engagement between the projections 13a and the recesses 13b permit relative pivotal movement between adjacent frame members 13 to assist in providing a smooth bending. Frame members 19 and 20 located at the opposite ends of the framework are only provided with either projection or recess since they are not engaged on the opposite side, and the ends of the flex 11 and the braided structure 15 are secured to these terminal frame members 19, 20. A flexure controlling wire or wires (not shown) are received in and passed through the depressions 11a (or 12a).

It should be noted that the skeleton, braided structure and frame member used in forming the bending tube of an endoscope according to the invention are not limited in configuraton and material to the specific illustration given above, but that certain changes and modifications can be made by one skilled in the art without departing from the spirit and scope of the invention as defined in the appended claims.

What is claimed is:

1. An endoscope comprising a distal end portion having an optical observation window, a control unit having an optical eye piece assembly; a flexible tube interconnecting the distal end portion and the control unit, said flexible tube internally housing a bundle of optical fibers which optically couples the observation window to the eye piece assembly; and a controllable bending tube interposed between the flexible tube and the distal end portion to enable bending of the distal end portion in at least a two-dimensional manner; said bending tube characterized by comprising an inner hollow cylindrical flexible braided structure capable of expanding and contracting and comprised of thin wires shown woven in crosswise pattern; said optical fiber bundle extending through said hollow braided structure; a flexible framework mounted concentric with and adjacent to the exterior surface of said braided structure and adapted to prevent the combined assembly of the braided structure and the flexible framework from being longitudinally compressed during bending and an outer plastic shell surrounding the exterior surface of said flexible framework.

2. An endoscope as set forth in claim 1, wherein said flexible framework comprises a flex.

3. An endoscope as set forth in claim 1, wherein said flexible framework comprises a plurality of hollow cylinders.

4. An endoscope as set forth in claim 3, wherein said hollow cylinders ar normally positioned in axial alignment; each of said hollow cylinders having a first end including projection means and another end including recess means, said projection means of a first hollow cylinder being received in and cooperating with said recess means of a next hollow cylinder to enable flexure of a series of hollow cylinders.

* * * * *